United States Patent

Gesellchen et al.

[11] 4,322,339
[45] Mar. 30, 1982

[54] PHARMACOLOGICALLY ACTIVE PEPTIDES

[75] Inventors: Paul D. Gesellchen, Indianapolis; Robert T. Shuman, Greenwood, both of Ind.

[73] Assignee: Eli Lilly and Company, Indianapolis, Ind.

[21] Appl. No.: 198,896

[22] Filed: Oct. 20, 1980

[51] Int. Cl.³ .......................................... C07C 103/52
[52] U.S. Cl. .................................... 260/112.5 E
[58] Field of Search ................... 260/112.5 E

[56] References Cited
FOREIGN PATENT DOCUMENTS

| | | |
|---|---|---|
| 2741393 | 8/1977 | Fed. Rep. of Germany ... 260/112.5 R |
| 770579 | 2/1977 | South Africa ............... 260/112.5 R |
| 774479 | 7/1977 | South Africa ............... 260/112.5 R |

OTHER PUBLICATIONS

Miller, et al., Vitamins and Hormones 36, Acad. Press, pp. 297–382, (1978).
Miller, "Structural Pharmacology and Neurobiology of the Enkephalins and Endorphins", 176th Amer. Chem. Soc. Nat'l. Mtg., Sep. 11–14, 1978, Miami Beach, Florida.
Meltzer, et al., Life Science 22, 1931–1938, (1978).

Primary Examiner—Delbert R. Phillips
Attorney, Agent, or Firm—William C. Martens; Arthur R. Whale

[57] ABSTRACT

Compounds of the formula

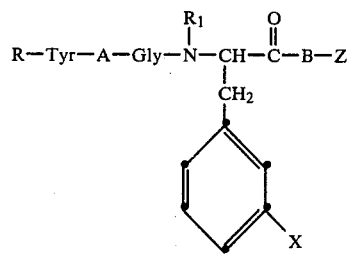

and pharmaceutically acceptable non-toxic acid addition salts thereof, in which R is hydrogen, methyl, or ethyl;
A is the residue of a D-amino acid selected from the group consisting of Ala, Abu, Nva, Val, Nle, Leu, Ile, Gly(Al), Gly(Cp), Met, Cys(Me), Met(O), Cys(Me) (O), Ser, Thr, and Hse;
$R_1$ is hydrogen, $C_1$–$C_3$ primary alkyl, cyclopropylmethyl, allyl, or propargyl;
X is bromo, iodo, chloro, $C_1$–$C_3$ alkyl, trifluoromethyl, or $C_1$–$C_2$ alkoxy;
B is the residue of a D- or L-amino acid lacking its carboxyl moiety and selected from the group consisting of Gly, Ala, Abu, Nva, Val, Nle, Leu, Ile, Pgl, Cys(Me), Cys(Me) ($O_2$), Cys(Me) ($O_2$), Cys(Et), Cys(Et) (O), Cys(Et) ($O_2$), Met, Met(O), Met($O_2$), Eth, Eth(O), Eth($O_2$), Ser(Me), Ser(Et), Hse(Me), and Hse(Et) as well as any of such residues substituted at the amino nitrogen by a $C_1$–$C_3$ primary alkyl;
Z is —$CH_2OR_2$,

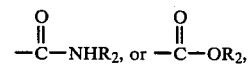

in which $R_2$ is hydrogen or $C_1$–$C_3$ alkyl; subject to the proviso that, when $R_1$ is other than hydrogen, B is the residue of an amino acid that lacks substitution at the amino nitrogen; are useful analgesic agents.

57 Claims, No Drawings

PHARMACOLOGICALLY ACTIVE PEPTIDES

BACKGROUND OF THE INVENTION

This invention relates to a novel class of compounds which exhibit analgesic activity.

Recently, endogenous substances having morphine-like properties have been extracted from mammalian brain or csf. These substances, named enkephalin, have been identified by Hughes et al., *Nature*, 258, 577 (1975) as pentapeptides having the following sequences:

H-Tyr-Gly-Gly-Phe-Met-OH
H-Tyr-Gly-Gly-Phe-Leu-OH.

These compounds are referred to as methionine-enkephalin and leucine-enkephalin, respectively.

Although methionine and leucine enkephalin have been shown to exhibit analgesic activity in mice upon administration intracerebroventricularly [Buscher et al., *Nature*, 261, 423 (1976)], they are practically devoid of any useful analgesic activity when administered parenterally.

Therefore, since the discovery of the enkephalins, much effort has been devoted to preparing analogs of the enkephalins in the hope of finding compounds having enhanced activity and practical utility due to their bioavailability by parenteral or oral administration.

Dutta et al., *Life Sciences* 21, pp. 559-562 (1977) report certain structure modifications which, they suggest, tend to enhance potency. They suggest activity can be enhanced by any or all of the following:

(a) substitution of Gly in position 2 by certain D- or α-aza-amino acids;

(b) conversion of the terminal carboxyl to the methyl ester or the amide;

(c) modification of the Phe in the 4-position by α-aza substitution, N-methylation, or hydrogenation of the aromatic ring.

In addition, Roemer et al., *Nature* 268, pp. 547-549 (1977), suggest modification of the $Met^5$ to its corresponding carbinol and oxidation of the Met sulfur to the sulfoxide as useful modifications.

Another structural modification of significance is that reported in Belgian Pat. No. 859,026. This publication suggests enhancement of activity and bioavailability of enkephalin analogs by insertion of a D-amino acid residue in position 2, conversion of the terminal carboxyl to an amide, and N-alkylation of the amino acid residue in position 5.

A class of analogs of enkephalin having a high level of analgesic activity has now been discovered. These analogs, in conjunction with their analgesic activity, exhibit a high level of binding at the enkephalin (δ) receptor compared with their binding characteristics at the morphine (μ) receptor. This class of analogs thus exhibits reduced morphine-like side effects. The increased enkephalin receptor activity also renders the analogs highly useful in the treatment of schizophrenia. These analogs are enkephalins having a ring-substituted phenylalanine. They are highly specific in terms both of the identity and the position of the substitution. In particular, they are pentapeptides having the residue of a meta-substituted L-phenylalanine in the 4-position of the peptide.

The literature recognizes other ring-substituted 4-phenylalanyl enkephalin analogs; however, they are not meta-substituted 4-phenylalanyl enkephalin analogs. A. R. Day et al., *Res. Comm. in Chem. Path. and Pharmacol.* 14 (4), 597-603 (1976) reports H-Tyr-Gly-Gly-pClPhe-Nle-OH. R. J. Miller et al., *Vitamins and Hormones* 36, 297-382, Academic Press (1978) mentions H-Tyr-D-Ala-Gly-pClPhe-D-Leu-OH; H-Tyr-D-Ala-Gly-pClPhe-D-Leu-OMe; and H-Tyr-D-Ala-Gly-pClPhe-D-Leu-NHEt. Pless et al., "Opioid Activity of Enkephalin Analogues," presented at the 15th European Peptide Symposium, Sept. 4-9, 1978, Gdansk, Poland, reports H-Tyr-D-Ala-Gly-pClPhe-Met(O)-ol. D. H. Coy et al., *BBRC* 83 (3), 977-983 (1978) mentions H-Tyr-D-Ala-Gly-$F_5$Phe-Met-$NH_2$. South African Pat. No. 77/0579 generically discloses pentapeptide enkephalin analogs variously substituted on the ring of the phenylanaline residue. U.S. application Ser. No. 104,348 filed Dec. 17, 1979, discloses and claims pentapeptide enkephalin analogs containing a p-fluoro-substituted phenylalanine.

None of the above reports the compounds of this invention, and it has been discovered that both the identity and position of the substituent on the L-phenylalanine play a significant role in the level of analgesic activity and associated properties of the enkephalin analog.

SUMMARY OF THE INVENTION

Thus, this invention relates to a class of compounds having the formula

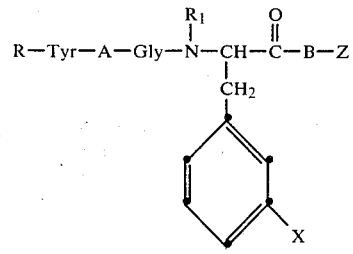

and pharmaceutically acceptable non-toxic acid addition salts thereof, in which

R is hydrogen, methyl, or ethyl;

A is the residue of a D-amino acid selected from the group consisting of Ala, Abu, Nva, Val, Nle, Leu, Ile, Gly(Al), Gly(Cp), Met, Cys(Me), Met(O), Cys(Me)(O), Ser, Thr, and Hse;

$R_1$ is hydrogen, $C_1$-$C_3$ primary alkyl, cyclopropylmethyl, allyl, or propargyl;

X is bromo, iodo, chloro, $C_1$-$C_3$ alkyl, trifluoromethyl, or $C_1$-$C_2$ alkoxy;

B is the residue of a D- or L-amino acid lacking its carboxyl moiety and selected from the group consisting of Gly, Ala, Abu, Nva, Val, Nle, Leu, Ile, Pgl, Cys(Me), Cys(Me)(O), Cys(Me)($O_2$), Cys(Et), Cys(Et)(O), Cys(Et)($O_2$), Met, Met(O), Met($O_2$), Eth, Eth(O), Eth($O_2$), Ser(Me), Ser(Et), Hse(Me), and Hse(Et) as well as any of such residues substituted at the amino nitrogen by a $C_1$-$C_3$ primary alkyl;

Z is —$CH_2OR_2$,

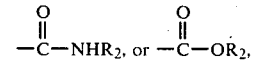

in which $R_2$ is hydrogen or $C_1$-$C_3$ alkyl; subject to the priviso, that, when $R_1$ is other than hydrogen, B is the residue of an amino acid that lacks substitution at the amino nitrogen.

DETAILED DESCRIPTION OF THE INVENTION

As indicated above, the compounds of this invention have the following structure:

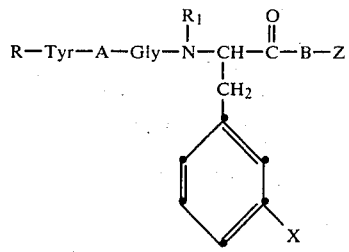

Also included are the pharmaceutically acceptable non-toxic acid addition salts of these compounds.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, formic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts are prepared by conventional methods.

As will be noted from the definition of the various substituents which appear in the above structure, the compounds which are defined by this structure are pentapeptides, the C-terminal portion of which is an acid, a primary alcohol or its lower alkyl ether derivative, a primary or secondary amide, or a lower alkyl ester.

The stereoconfiguration of the compounds of this invention is an essential feature thereof. For the sake of convenience, the amino acid residues of the pentapeptides of this invention are numbered sequentially beginning with the residue at the terminal amino function. The chirality of the amino acid residues, reading from Position 1 through Position 4, is L, D, none, and L. The residue in Position 3 is a glycine moiety, and, thus, no chirality as to this residue exists. As to Position 5 (the C-terminal position), its chirality is defined as that which is consistent with and corresponds to the corresponding putative L-amino acid residue or the corresponding putative D-amino acid residue, as well as, of course, the racemic mixture of both.

The group $R_1$ and the amino substitutent of B is defined to include the group "$C_1$-$C_3$ primary alkyl". By the term "$C_1$-$C_3$ primary alkyl" is meant methyl, ethyl, and n-propyl.

The groups $R_2$ and X as used herein are defined to include the group "$C_1$-$C_3$ alkyl". By the term "$C_1$-$C_3$ alkyl" is intended methyl, ethyl, n-propyl and isopropyl.

The group X as used herein is defined to include the group "$C_1$-$C_2$ alkoxy". By the term "$C_1$-$C_2$ alkoxy" is intended methoxy and ethoxy.

With respect to the particular position residues of the pentapeptides of this invention, the following considerations prevail:

(A) Position 1.

This position represents the amino-terminal portion of the peptide. The residue is that which results from L-tyrosine. The residue can be N-unsubstituted, in which case R is hydrogen. Moreover, the residue can be N-mono-substituted, giving rise to N-methyl or N-ethyl. For compounds having exceptionally high levels of analgesic activity when administered parenterally, the tyrosyl residue which is present in Position 1 preferably is N-unsubstituted. For compounds having exceptionally high levels of analgesic activity when administered orally, the tyrosyl residue which is present in Position 1 preferably is N-substituted. In the event that the tyrosyl is N-substituted, the N-substituent preferably is methyl.

(B) Position 2.

The amino acid residue (A) which is present in the second position of the peptides of this invention must be the D stereoisomer and is any of several amino acid residues, depending upon the substituent ($R_3$) on the α-carbon. These include residues derived from D-alanine (Ala) ($R_3$ is methyl), D-α-aminobutyric acid (Abu) ($R_3$ is ethyl), D-norvaline (Nva) ($R_3$ is n-propyl), D-valine (Val) ($R_3$ is isopropyl), D-norleucine (Nle) ($R_3$ is n-butyl), D-leucine (Leu) ($R_3$ is isobutyl), D-isoleucine (Ile) ($R_3$ is sec-butyl), D-allylglycine [Gly(Al)] ($R_3$ is allyl), D-cyclopropylmethylglycine [Gly(Cp)] ($R_3$ is cyclopropylmethyl), D-methionine (Met) ($R_3$ is 2-methylthioethyl), D-(S-methyl)cysteine [Cys(Me)] ($R_3$ is methylthiomethyl), D-methionine sulfoxide [Met(O)] ($R_3$ is methylsulfinylethyl), D-(S-methyl)cysteine sulfoxide [Cys(Me)(O)] ($R_3$ is methylsulfinylmethyl), D-serine (Ser) ($R_3$ is hydroxymethyl), D-threonine (Thr) ($R_3$ is 1-hydroxyethyl), and D-homoserine (Hse) ($R_3$ is 2-hydroxyethyl). Preferably, A is Ala, Abu, Nva, Val, Nle, Leu, Ile, Ser, Thr, or Hse; and, more preferably, is Ala, Abu, Nva, Val, Nle, Leu, or Ile. Most preferably, A is Ala.

(C) Position 3.

The amino acid residue present in this position is that derived from glycine (Gly).

(D) Position 4

The amino acid residue present in this position is that derived from meta-substituted L-phenylalanine [Phe(X)]. The group X represents the meta substituent and is any of bromo, iodo, chloro, $C_1$-$C_3$ alkyl, trifluoromethyl, and $C_1$-$C_2$ alkoxy. Preferably, X is bromo, iodo, or chloro, and, most preferably, is bromo or chloro.

The residue can be either unsubstituted or substituted at the amino nitrogen ($R_1$). In the event that the residue is N-substituted, it is N-methyl, N-ethyl, N-n-propyl, N-propargyl, N-cyclopropylmethyl, or N-allyl. Preferably, when $R_1$ is other than hydrogen, it is $C_1$-$C_3$ primary alkyl, and, if the latter, methyl or ethyl.

(E) Position 5.

The residue (—B—Z) present in the C-terminal position of the compounds of this invention is an amino acid structurally derivatized to its amide

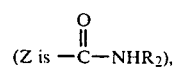

(Z is —C—NHR$_2$), its primary alcohol or corresponding $C_1$-$C_3$ alkyl ether (Z is —CH$_2$OR$_2$), or its acid or $C_1$-$C_3$ alkyl ester

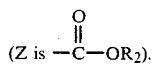
(Z is).

The chirality of the amino acid residue in Position 5 of the pentapeptide is the L-, the D-, or the D,L-mixture. Preferably, the chirality of the amino acid residue is L-. The group —B—Z is any of several amino acid residues, depending upon the substituent ($R_4$) on the $\alpha$-carbon. These include residues derived from glycine (Gly) ($R_4$ is hydrogen), alanine (Ala) ($R_4$ is methyl), $\alpha$-aminobutyric acid (Abu) ($R_4$ is ethyl), norvaline (Nva) ($R_4$ is n-propyl), valine (Val) ($R_4$ is isopropyl), norleucine (Nle) ($R_4$ is n-butyl), leucine (Leu) ($R_4$ is isobutyl), isoleucine (Ile) ($R_4$ is sec-butyl), phenylglycine (Pgl) ($R_4$ is phenyl), (S-methyl)cysteine [Cys(Me)] ($R_4$ is methylthiomethyl), (S-methyl)cysteine sulfoxide [Cys(Me)(O)] ($R_4$ is methylsulfinylmethyl), (S-methyl)cysteine sulfone [Cys(Me)($O_2$)] ($R_4$ is methylsulfonylmethyl), (S-ethyl)cysteine [Cys(Et)] ($R_4$ is ethylthiomethyl), (S-ethyl)cysteine sulfoxide [Cys(Et)(O)] ($R_4$ is ethylsulfinylmethyl), (S-ethyl)cysteine sulfone [Cys(Et)($O_2$)] ($R_4$ is ethylsulfonylmethyl), methionine (Met) ($R_4$ is methylthioethyl), methionine sulfoxide [Met(O)] ($R_4$ is methylsulfinylethyl), methionine sulfone [Met($O_2$)] ($R_4$ is methylsulfonylethyl), ethionine (Eth) ($R_4$ is ethylthioethyl), ethionine sulfoxide [Eth(O)] ($R_4$ is ethylsulfinylethyl), ethionine sulfone [Eth($O_2$)] ($R_4$ is ethylsulfonylethyl), (O-methyl)serine [Ser(Me)] ($R_4$ is methoxymethyl), (O-ethyl)serine [Ser(Et)] ($R_4$ is ethoxymethyl), (O-methyl)homoserine [Hse(Me)] ($R_4$ is methoxyethyl), and (O-ethyl)homoserine [Hse(Et)] ($R_4$ is ethoxyethyl).

A preferred subclass of compounds is that in which the terminal amino acid residue is Ala, Abu, Nva, Val, Nle, Leu, or Ile. Of these, those compounds in which the terminal amino acid residue is Leu are especially preferred.

Another preferred subclass of compounds is that in which the terminal amino acid residue is Cys(Me), Cys(Me)(O), Cys(Me)($O_2$), Cys(Et), Cys(Et)(O), Cys(Et)($O_2$), Met, Met(O), Met($O_2$), Eth, Eth(O), Eth($O_2$), Ser(Me), Ser(Et), Hse(Me), or Hse(Et). Of these, those compounds in which the terminal amino acid residue is Met are especially preferred.

Another preferred subclass of compounds is that in which the terminal amino acid residue is Pgl unsubstituted at the amino nitrogen.

The terminal amino acid residue is either unsubstituted or substituted at its amino nitrogen. In those instances in which a substituent is present, the substituent is a $C_1$-$C_3$ primary alkyl group. The represented substituents are N-methyl, N-ethyl, and N-n-propyl. Preferably, the amino nitrogen is substituted, and, more preferably, the substituent is methyl. Furthermore, when the terminal amino acid residue is substituted at its amino nitrogen, $R_1$ must be hydrogen, and when $R_1$ is other than hydrogen, the terminal amino acid residue must be unsubstituted at its amino nitrogen.

In addition, as already noted, the residue in Position 5 is an amide, a primary alcohol, an ether, an acid, or an ester. Preferably, the residue is an amide, an alcohol, or an ester, and, more preferably, is an amide. Of the latter, the residue preferably is a primary amide, i.e., Z is

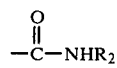

and $R_2$ is hydrogen. When the amide is a secondary amide, $R_2$ is a $C_1$-$C_3$ alkyl group. In those instances, the terminal amide group is N-methyl, N-ethyl, N-n-propyl, or N-isopropyl; preferably, it is N-methyl.

In this specification, the following abbreviations, most of which are well known and are commonly used in the art, are employed:
Abu—$\alpha$-aminobutyric acid
Ala—alanine
Cys(Et)—(S-ethyl)cysteine
Cys(Et)(O)—(S-ethyl)cysteine sulfoxide
Cys(Et)($O_2$)—(S-ethyl)cysteine sulfone
Cys(Me)—(S-methyl)cysteine
Cys(Me)(O)—(S-methyl)cysteine sulfoxide
Cys(Me)($O_2$)—(S-methyl)cysteine sulfone
Eth—ethionine
Eth(O)—ethionine sulfoxide
Eth($O_2$)—ethionine sulfone
Gly—glycine
Gly(Al)—allylglycine
Gly(Cp)—cyclopropylmethylglycine
Hse—homoserine
Hse(Me)—(O-methyl)homoserine
Hse(Et)—(O-ethyl)homoserine
Ile—isoleucine
Leu—leucine
Met—methionine
Met(O)—methionine sulfoxide
Met($O_2$)—methionine sulfone
Nle—norleucine
Nva—norvaline
Pgl—phenylglycine
Phe—phenylalanine
Ser—serine
Ser(Me)—(O-methyl)serine
Ser(Et)—(O-ethyl)serine
Thr—threonine
Tyr—tyrosine
Val—valine
Ac—acetyl
Al—allyl
Cp—cyclopropylmethyl
Me—methyl
Et—ethyl
Ip—isopropyl
Pr—n-propyl
Ppg—propargyl
MeO—methoxy
EtO—ethoxy
Boc—t-butyloxycarbonyl
Bzl—benzyl
DCC—N,N'-dicyclohexylcarbodiimide
HBT—1-hydroxybenzotriazole
DMF—N,N-dimethylformamide
TFA—trifluoroacetic acid
THF—tetrahydrofuran
DEAE—diethylaminoethyl
IBCF—isobutyl chloroformate
NMM—N-methylmorpholine
18-crown-6—1,4,7,10,13,16-hexaoxacyclooctadecane Examples of typical compounds of this invention include the following, each of which carries a substituent in the meta position of the phenylalanine and any or all of which may be in the form of a pharmaceutically acceptable non-toxic acid addition salt:

H-L-Tyr-D-Ala-Gly-L-(N-Me)Phe(Br)-L-Met-NH$_2$;
H-L-Tyr-D-Ala-Gly-L-Phe(I)-L-(N-Me)Met-NH$_2$;
H-L-Tyr-D-Abu-Gly-L-Phe(Cl)-L-(N-Et)Met-NH$_2$;
H-L-Tyr-D-Abu-Gly-L-Phe(Br)-D-(N-Me)Met-NH$_2$;
H-L-Tyr-D-Nva-Gly-L-Phe(MeO)-L-(N-Me)Met-NH$_2$;
H-L-Tyr-D-Nva-Gly-L-(N-Et)Phe(Me)-L-Met-NH$_2$;
H-L-Tyr-D-Val-Gly-L-Phe(Et)-D-(N-Et)Met-NH$_2$;
H-L-Tyr-D-Val-Gly-L-(N-Pr)Phe(Pr)-L-Met-NH$_2$;
H-L-Tyr-D-Nle-Gly-L-Phe(Ip)-L-(N-Me)Met-NH$_2$;
H-L-Tyr-D-Nle-Gly-L-Phe(CF$_3$)-D-(N-Et)Gly-NH$_2$;
H-L-Tyr-D-Leu-Gly-L-(N-Ppg)Phe(MeO)-L-Met-NH$_2$;
H-L-Tyr-D-Leu-Gly-L-Phe(EtO)-L-(N-Pr)Met-NH$_2$;
H-L-Tyr-D-Ile-Gly-L-Phe(Br)-L-(N-Me)Met-NH$_2$;
H-L-Tyr-D-Ile-Gly-L-Phe(I)-D-(N-Pr)Met-NH$_2$;
H-L-Tyr-D-Ala-Gly-L-Phe(Cl)-L-(N-Et)Met-NH$_2$;
H-L-Tyr-D-Ala-Gly-L-Phe(Br)-L-(N-Pr)Met-NH$_2$;
H-L-Tyr-D-Ala-Gly-L-Phe(Cl)-D-(N-Pr)Met-NH$_2$;
H-L-Tyr-D-Ala-Gly-L-(N-Ppg)Phe(Br)-L-Met-NH$_2$;
H-L-Tyr-D-Ala-Gly-L-Phe(Br)-L-(N-Me)Met-NH$_2$;
H-L-Tyr-D-Ala-Gly-L-(N-Ppg)Phe(I)-D-Met-NH$_2$;
H-L-Tyr-D-Ala-Gly-L-Phe(Me)-L-(N-Me)Ala-NH$_2$;
H-L-Tyr-D-Ala-Gly-L-Phe(Pr)-L-(N-Me)Abu-NH$_2$;
H-L-Tyr-D-Ala-Gly-L-Phe(Cl)-L-(N-Et)Nva-NH$_2$;
H-L-Tyr-D-Ala-Gly-L-Phe(CF$_3$)-D-(N-Et)Val-NH$_2$;
H-L-Tyr-D-Val-Gly-L-Phe(EtO)-L-(N-Me)Nle-NH$_2$;
H-L-Tyr-D-Leu-Gly-L-Phe(MeO)-L-(N-Me)Leu-NH$_2$;
H-L-Tyr-D-Val-Gly-L-Phe(Br)-L-(N-Et)Ile-NH$_2$;
H-L-Tyr-D-Leu-Gly-L-(N-Me)Phe(Et)-D-Pgl-NH$_2$;
H-L-Tyr-D-Ala-gly-L-(N-Cp)Phe(Br)-L-Nle-NH$_2$;
H-L-Tyr-D-Ala-Gly-L-Phe(Cl)-L-(N-Et)Hse(Me)-NH$_2$;
H-L-Tyr-D-Ala-Gly-L-(N-Me)Phe(I)-L-Pgl-NH$_2$;
H-L-Tyr-D-Ala-Gly-L-Phe(Br)-D-(N-Me)Hse(Me)-NH$_2$;
H-L-Tyr-D-Ala-Gly-L-(N-Al)Phe(I)-L-Met-NH$_2$;
H-L-Tyr-D-Gly(Al)-Gly-L-Phe(Br)-L-(N-Me)Met-NH$_2$;
H-L-Tyr-D-Gly(Cp)-Gly-L-Phe(Br)-L-Pgl-NH$_2$;
H-L-Tyr-D-Met-Gly-L-Phe(Cl)-L-(N-Me)Met-NH$_2$;
H-L-Tyr-D-Cys(Me)-Gly-L-Phe(I)-D-(N-Et)Met-NH$_2$;
H-L-Tyr-D-Met(O)-Gly-L-Phe(Br)-L-(N-Et)Met-NH$_2$;
H-L-Tyr-D-Cys(Me)(O)-Gly-L-Phe(Cl)-L-Pgl-NH$_2$;
H-L-Tyr-D-Ser-Gly-L-Phe(CF$_3$)-L-(N-Me)Hse(Me)-NH$_2$;
H-L-Tyr-D-Ala-Gly-L-(N-Et)-Phe(EtO)-L-Pgl-NH$_2$;
H-L-Tyr-D-Ala-Gly-L-Phe(MeO)-L-(N-Me)Pgl-NH$_2$;
H-L-Tyr-D-Thr-Gly-L-(N-Et)Phe(Br)-L-Met-NH$_2$;
H-L-Tyr-D-Hse-Gly-L-Phe(I)-L-(N-Me)Met-NH$_2$;
(N-Me)-L-Tyr-D-Ala-Gly-L-Phe(Cl)-L-(N-Me)-Cys(-Me)-NH$_2$;
H-L-Tyr-D-Ala-Gly-L-Phe(I)-L-(N-Me)Cys(Me)-(O)-NH$_2$;
H-L-Tyr-D-Ala-Gly-L-Phe(Br)-D-(N-Me)Cys(Et)-NH$_2$;
(N-Et)-L-Tyr-D-Abu-Gly-L-Phe(Cl)-L-(N-Et)-Nle-NH$_2$;
H-L-Tyr-D-Val-Gly-L-(N-Et)Phe(Cl)-L-Hse(Me)-NH$_2$;
(N-Me)-L-Tyr-D-Leu-Gly-L-Phe(Br)-L-(N-Me)-Cys-(Et)(O$_2$)-NH$_2$;
H-L-Tyr-D-Abu-Gly-L-Phe(Cl)-L-(N-Pr)Met(O)-NH$_2$;
H-L-Tyr-D-Nle-Gly-L-Phe(CF$_3$)-L-(N-Me)Eth-NH$_2$;
H-L-Tyr-D-Ile-Gly-L-Phe(MeO)-D-(N-Pr)Eth(O)-NH$_2$;
(N-Me)-L-Tyr-D-Leu-Gly-L-Phe(Me)-L-(N-Et)-Nle-NH$_2$;
(N-Me)-L-Tyr-D-Nva-Gly-L-Phe(Br)-L-(N-Me)Hse(Et)-NH$_2$;
(N-Me)-L-Tyr-D-Ala-Gly-L-(N-Et)Phe(Cl)-D-Ser(-Me)-NH$_2$;
H-L-Tyr-D-Ala-Gly-L-(N-Me)Phe(I)-L-Ser(Et)-NH$_2$;
H-L-Tyr-D-Ala-Gly-L-(N-Me)Phe(I)-D-Leu-NH$_2$;
H-L-Tyr-D-Ala-Gly-L-(N-Et)Phe(Br)-L-Pgl-NH$_2$;
H-L-Tyr-D-Ala-Gly-L-(N-Al)Phe(Br)-L-Leu-NH$_2$;
H-L-Tyr-D-Ala-Gly-L-(N-Pr)Phe(I)-L-Pgl-NH$_2$;
H-L-Tyr-D-Ala-Gly-L-(N-Me)Phe(I)-L-Met-NH$_2$;
H-L-Tyr-D-Ala-Gly-L-(N-et)Phe(Cl)-L-Met(O$_2$)-NH$_2$;
H-L-Tyr-D-Ala-Gly-L-(N-Et)Phe(Ip)-L-Met-NH(Me);
H-L-Tyr-D-Ala-Gly-L-Phe(Pr)-L-(N-Me)Met-NH(Me);
H-L-Tyr-D-Ala-Gly-L-Phe(Br)-L-(N-Et)Met-NH(Me);
H-L-Tyr-D-Ala-Gly-L-Phe(Cl)-L-(N-Me)Met-NH(Et);
H-L-Tyr-D-Ala-Gly-L-(N-Et)Phe(Et)-L-Met-NH(Et);
H-L-Tyr-D-Ala-Gly-L-Phe(EtO)-L-(N-Me)Nle-NH(Me);
H-L-Tyr-D-Ala-Gly-L-Phe(Cl)-L-(N-Et)Pgl-NH(Pr);
H-L-Tyr-D-Ala-Gly-L-Phe(I)-L-(N-Pr)Leu-NH(Me);
H-L-Tyr-D-Ala-Gly-L-(N-Al)Phe(Br)-L-Met-NH(Ip);
H-L-Tyr-D-Ala-Gly-L-(N-Me)Phe(Br)-L-Met-CH$_2$OH;
H-L-Tyr-D-Ala-Gly-L-Phe(I)-L-(N-Me)Met-CH$_2$OH;
H-L-Tyr-D-Abu-Gly-L-Phe(Cl)-L-(N-Et)Met-CH$_2$OH;
H-L-Tyr-D-Abu-Gly-L-Phe(EtO)-D-(N-Me)Met-CH$_2$OH;
H-L-Tyr-D-Nva-Gly-L-Phe(CF$_3$)-L-(N-Me)Met-CH$_2$OH;
H-L-Tyr-D-Nva-Gly-L-(N-Et)Phe(Br)-L-Met-CH$_2$OH;
H-L-Tyr-D-Val-Gly-L-Phe(I)-D-(N-Et)Met-CH$_2$OH;
H-L-Tyr-D-Val-Gly-L-(N-Pr)Phe(Cl)-L-Met-CH$_2$OH;
H-L-Tyr-D-Nle-Gly-L-Phe(Me)-L-(N-Me)Met-CH$_2$OH;
H-L-Tyr-D-Nle-Gly-L-Phe(MeO)-D-(N-Et)Gly-CH$_2$OH;
H-L-Tyr-D-Leu-Gly-L-(N-Ppg)Phe(Br)-L-Met-CH$_2$OH;
H-L-Tyr-D-Leu-Gly-L-Phe(I)-L-(N-Pr)Met-CH$_2$OH;
H-L-Tyr-D-Ile-Gly-L-Phe(Cl)-L-(N-Me)Met-CH$_2$OH;
H-L-Tyr-D-Ile-Gly-L-Phe(Br)-D-(N-Pr)Met-CH$_2$OH;
H-L-Tyr-D-Ala-Gly-L-Phe(Et)-L-(N-Et)Met-CH$_2$OH;
H-L-Tyr-D-Ala-Gly-L-Phe(EtO)-L-(N-Pr)Met-CH$_2$OH;
H-L-Tyr-D-Ala-Gly-L-Phe(CF$_3$)-D-(N-Pr)Met-CH$_2$OH;
H-L-Tyr-D-Ala-Gly-L-(N-Ppg)Phe(Br)-L-Met-(O$_2$)-CH$_2$OH;
H-L-Tyr-D-Ala-Gly-L-Phe(I)-L-(N-Me)Met-CH$_2$OH;
H-L-Tyr-D-Ala-Gly-L-(N-Ppg)Phe(I)-D-Met-CH$_2$OH;
H-L-Tyr-D-Ala-Gly-L-Phe(Cl)-L-(N-Me)Ala-CH$_2$OH;
H-L-Tyr-D-Ala-Gly-L-Phe(Br)-L-(N-Me)Abu-CH$_2$OH;
H-L-Tyr-D-Ala-Gly-L-Phe(Cl)-L-(N-Et)Nva-CH$_2$OH;

H-L-Tyr-D-Ala-Gly-L-Phe(I)-D-(N-Et)Val-CH₂OH;
H-L-Tyr-D-Val-Gly-L-Phe(Br)-L-(N-Me)Nle-CH₂OH;
H-L-Tyr-D-Leu-Gly-L-Phe(Me)-L-(N-Me)Leu-CH₂OH;
H-L-Tyr-D-Val-Gly-L-Phe(Et)-L-(N-Et)Ile-CH₂OH;
H-L-Tyr-D-Leu-Gly-L-Phe(MeO)-D-Pgl-CH₂OH;
H-L-Tyr-D-Ala-Gly-L-(N-Cp)Phe(CF₃)-L-Nle-CH₂OH;
H-L-Tyr-D-Ala-Gly-L-Phe(Br)-L-(N-Et)Hse(Me)-CH₂OH;
H-L-Tyr-D-Ala-Gly-L-Phe(Br)-L-Pgl-CH₂OH;
H-L-Tyr-D-Ala-Gly-L-Phe(I)-D-(N-Me)Hse-(Me)-CH₂OH;
H-L-Tyr-D-Ala-Gly-L-(N-Al)Phe(Br)-L-Met-CH₂OH;
H-L-Tyr-D-Gly(Al)-Gly-L-Phe(Cl)-L-(N-Me)Met-CH₂OH;
H-L-Tyr-D-Gly(Cp)-Gly-L-Phe(Br)-L-Pgl-CH₂OH;
H-L-Tyr-D-Met-Gly-L-Phe(I)-L-(N-Me)Met-CH₂OH;
H-L-Tyr-D-Cys(Me)-Gly-L-Phe(Pr)-D-(N-Et)Met-CH₂OH;
H-L-Tyr-D-Met(O)-Gly-L-Phe(Br)-L-(N-Et)Met-CH₂OH;
H-L-Tyr-D-Cys(Me)(O)-Gly-L-Phe(I)-L-(N-Me)Met-CH₂OH;
H-L-Tyr-D-Ser-Gly-L-Phe(Cl)-L-(N-Me(Hse-(Me)-CH₂OH;
H-L-Tyr-D-Ala-Gly-L-(N-Et)Phe(Me)-L-Pgl-CH₂OH;
H-L-Tyr-D-Ala-Gly-L-Phe(CF₂)-L-Pgl-CH₂OH;
H-L-Tyr-D-Thr-Gly-L-(N-Et)Phe(MeO)-L-Met-CH₂OH;
H-L-Tyr-D-Hse-Gly-L-Phe(EtO)-L-(N-Me)Met-CH₂OH;
(N-Me)-L-Tyr-D-Ala-Gly-L-Phe(Ip)-L-(N-Me)Cys(-Me)-CH₂OH;
H-L-Tyr-D-Ala-Gly-L-Phe(Pr)-L-(N-Me)-Cys(Me)-(O)-CH₂OH;
H-L-Tyr-D-Ala-Gly-L-Phe(Br)-D-(N-Me)Cys(Et)-(O₂)-CH₂OH;
(N-Et)-L-Tyr-D-Abu-Gly-L-Phe(Br)-L-(N-Et)-Nle-CH₂OH;
H-L-Tyr-D-Val-Gly-L-(N-Et)Phe(I)-L-Hse(Me)-CH₂OH;
(N-Me)-L-Tyr-D-Leu-Gly-L-Phe(Cl)-L-(N-Me)Cys-(Et)(O)-CH₂OH;
H-L-Tyr-D-Abu-Gly-L-Phe(Ip)-L-(N-Pr)Met(O)-CH₂OH;
H-L-Tyr-D-Nle-Gly-L-Phe(Br)-L-(N-Me)Eth-CH₂OH;
H-L-Tyr-D-Ile-Gly-L-Phe(I)-D-(N-Pr)Eth(O₂)-CH₂OH;
(N-Me)-L-Tyr-D-Leu-Gly-L-Phe(I)-L-(N-Et)-Nle-CH₂OH;
(N-Me)-L-Tyr-D-Nva-Gly-L-Phe(Cl)-L-(N-Me)Hse(Et)-CH₂OH;
(N-Me)-L-Tyr-D-Ala-Gly-L-(N-Et)Phe(Br)-D-Ser(-Me)-CH₂OH;
H-L-Tyr-D-Ala-Gly-L-(N-Me)Phe(Me)-L-Ser(Et)-CH₂OH;
H-L-Tyr-D-Ala-Gly-L-(N-Me)Phe(Et)-D-Leu-CH₂OH;
H-L-Tyr-D-Ala-Gly-L-(N-Et)Phe(Pr)-L-Pgl-CH₂OH;
H-L-Tyr-D-Ala-Gly-L-(N-Al)Phe(Ip)-L-Leu-CH₂OH;
H-L-Tyr-D-Ala-Gly-L-(N-Pr)Phe(CF₃)-L-Pgl-CH₂OH;
H-L-Tyr-D-Ala-Gly-L-(N-Me)Phe(MeO)-L-Met-CH₂OH;
H-L-Tyr-D-Ala-Gly-L-(N-Et)Phe(EtO)-L-Met(O)-CH₂OH;
H-L-Tyr-D-Ala-Gly-L-(N-Et)Phe(Cl)-L-Met-CH₂OMe;
H-L-Tyr-D-Ala-Gly-L-Phe(Br)-L-(N-Me)Met-CH₂OMe;
H-L-Tyr-D-Ala-Gly-L-Phe(Cl)-L-(N-Et)Met-CH₂OMe;
H-L-Tyr-D-Ala-Gly-L-Phe(I)-L-(N-Me)Met-CH₂OEt;
H-L-Tyr-D-Ala-Gly-L-(N-Et)Phe(Br)-L-Met-CH₂OEt;
H-L-Tyr-D-Ala-Gly-L-Phe(I)-L-(N-Me)Nle-CH₂OMe;
H-L-Tyr-D-Ala-Gly-L-Phe(Br)-L-(N-Et)Pgl-CH₂OPr;
H-L-Tyr-D-Ala-Gly-L-Phe(Cl)-L-(N-Pr)Leu-CH₂OMe;
H-L-Tyr-D-Ala-Gly-L-(N-Al)Phe(I)-L-Met-CH₂OIp;
H-L-Tyr-D-Ala-Gly-L-(N-Me)Phe(Br)-L-Met-OMe;
H-L-Tyr-D-Ala-Gly-L-Phe(Cl)-L-(N-Me)Met-OEt;
H-L-Tyr-D-Abu-Gly-L-Phe(Me)-L-(N-Et)Met-OMe;
H-L-Tyr-D-Abu-Gly-L-Phe(Et)-D-(N-Me)Met-OMe;
H-L-Tyr-D-Nva-Gly-L-Phe(EtO)-L-(N-Me)Met-OPr;
H-L-Tyr-D-Nva-Gly-L-(N-Et)Phe(CF₃)-L-Met-OH;
H-L-Tyr-D-Val-Gly-L-Phe(Br)-D-(N-Et)Met-OMe;
H-L-Tyr-D-Val-Gly-L-(N-Pr)Phe(Br)-L-Met-OH;
H-L-Tyr-D-Nle-Gly-L-Phe(I)-L-(N-Me)Met-OEt;
H-L-Tyr-D-Nle-Gly-L-Phe(Cl)-D-(N-Et)Gly-OMe;
H-L-Tyr-D-Leu-Gly-L-(N-Ppg)Phe(Br)-L-Met-OH;
H-L-Tyr-D-Leu-Gly-L-Phe(Pr)-L-(N-Pr)Met-OPr;
H-L-Tyr-D-Ile-Gly-L-Phe(Ip)-L-(N-Me)Met-OMe;
H-L-Tyr-D-Ile-Gly-L-Phe(Br)-D-(N-Pr)Met-OMe;
H-L-Tyr-D-Ala-Gly-L-Phe(I)-L-(N-Et)Met-OMe;
H-L-Tyr-D-Ala-Gly-L-Phe(Cl)-L-(N-Pr)Met-OH;
H-L-Tyr-D-Ala-Gly-L-Phe(Br)-D-(N-Pr)Met(O₂)-OH;
H-L-Tyr-D-Ala-Gly-L-(N-Ppg)Phe(Br)-L-Met-OMe;
H-L-Tyr-D-Ala-Gly-L-Phe(I)-L-(N-Me)Met-OH;
H-L-Tyr-D-Ala-Gly-L-(N-Ppg)Phe(Cl)-D-Met-OEt;
H-L-Tyr-D-Ala-Gly-L-Phe(Cl)-L-(N-Me)Ala-OPr;
H-L-Tyr-D-Ala-Gly-L-Phe(Br)-L-(N-Me)Abu-OIp;
H-L-Tyr-D-Ala-Gly-L-Phe(I)-L-(N-Et)Nva-OMe;
H-L-Tyr-D-Ala-Gly-L-Phe(Br)-D-(N-Et)Val-OMe;
H-L-Tyr-D-Val-Gly-L-Phe(Cl)-L-(N-Me)Nle-OMe;
H-L-Tyr-D-Leu-Gly-L-Phe(I)-L-(N-Me)Leu-OEt;
H-L-Tyr-D-Val-Gly-L-Phe(Et)-L-(N-Et)Ile-OH;
H-L-Tyr-D-Leu-Gly-L-Phe(EtO)-D-(N-Me)Met-OEt;
H-L-Tyr-D-Ala-Gly-L-(N-Cp)Phe(Me)-L-Nle-OPr;
H-L-Tyr-D-Ala-Gly-L-Phe(MeO)-L-(N-Et)Hse-(Me)-OIp;
H-L-Tyr-D-Ala-Gly-L-Phe(I)-L-(N-Me)Pgl-OMe;
H-L-Tyr-D-Ala-Gly-L-Phe(Ip)-D-(N-Me)Hse(Me)-OH;
H-L-Tyr-D-Ala-Gly-L-(N-Al)Phe(Pr)-L-Met-OEt;
H-L-Tyr-D-Gly(Al)-Gly-L-Phe(Me)-L-(N-Me)Met-OEt;
H-L-Tyr-D-Gly(Cp)-Gly-L-Phe(Et)-L-(N-Me)-Pgl-OPr;
H-L-Tyr-D-Met-Gly-L-Phe(I)-L-(N-Me)Met-OMe;
H-L-Tyr-D-Cys(Me)-Gly-L-Phe(Cl)-D-(N-Et)Met-OH;
H-L-Tyr-D-Met(O)-Gly-L-Phe(I)-L-(N-Et)Met-OIp;
H-L-Tyr-D-Cys(Me)(O)-Gly-L-Phe(Br)-L-(N-Me)-Met-OH;
H-L-Tyr-D-Ser-Gly-L-Phe(Br)-L-(N-Me)Hse(Me)-OEt;
H-L-Tyr-D-Ala-Gly-L-(N-Et)Phe(Cl)-L-Pgl-OEt;
H-L-Tyr-D-Ala-Gly-L-Phe(I)-L-(N-Me)Pgl-OEt;
H-L-Tyr-D-Thr-Gly-L-(N-Et)Phe(Cl)-L-Met-OMe;
H-L-Tyr-D-Hse-Gly-L-Phe(Br)-L-(N-Me)Met-OH;

(N-Me)-L-Tyr-D-Ala-Gly-L-Phe(Cl)-L-(N-Me)Cys(-Me)-OMe;
H-L-Tyr-D-Ala-Gly-L-Phe(I)-L-(N-Me)-Cys(Me)(O)-OH;
H-L-Tyr-D-Ala-Gly-L-Phe(Br)-D-(N-Me)Cys(Et)-OMe;
(N-Et)-L-Tyr-D-Abu-Gly-L-Phe(Br)-L-(N-Et)Nle-OEt;
H-L-Tyr-D-Val-Gly-L-(N-Et)Phe(Me)-L-Hse(Me)-OMe;
(N-Me)-L-Tyr-D-Leu-Gly-L-Phe(Et)-L-(N-Me)-Cys(et)(O)-OH;
H-L-Tyr-D-Abu-Gly-L-Phe(CF$_3$)-L-(N-Pr)Met(O)-OMe;
H-L-Tyr-D-Nle-Gly-L-Phe(Br)-L-(N-Me)Eth-OEt;
H-L-Tyr-D-Ile-Gly-L-Phe(Pr)-D-(N-Pr)Eth(O)-OPr;
(N-Me)-L-Tyr-D-Leu-Gly-L-Phe(Ip)-L-(N-Et)-Nle-OIp;
(N-Me)-L-Tyr-D-Nva-Gly-L-Phe(MeO)-L-(N-Me)Hse(Et)-OH;
(N-Me)-L-Tyr-D-Ala-Gly-L-(N-Et)Phe(EtO)-D-Ser(-Me)-OPr;
H-L-Tyr-D-Ala-Gly-L-(N-Me)Phe(Br)-L-Ser(Et)-OMe;
H-L-Tyr-D-Ala-Gly-L-(N-Me)Phe(I)-D-Leu-OEt;
H-L-Tyr-D-Ala-Gly-L-(N-Et)Phe(Cl)-L-Pgl-OH;
H-L-Tyr-D-Ala-Gly-L-(N-Al)Phe(Cl)-L-Leu-OMe;
H-L-Tyr-D-Ala-Gly-L-(N-Pr)Phe(Br)-L-Pgl-OMe;
H-L-Tyr-D-Ala-Gly-L-(N-Me)Phe(I)-L-Met-OMe;
H-L-Tyr-D-Ala-Gly-L-(N-Et)Phe(Br)-L-Met(O$_2$)-OH;
and the like.

The compounds of this invention are prepared by routine methods for peptide synthesis. It is possible, during the synthesis of certain of the compounds of this invention, that partial racemization can occur. However, the extent of racemization, should such occur, is not sufficient to significantly alter the analgesic activity of the compounds of this invention.

The compounds of this invention can be synthesized by solid phase peptide synthesis or by classical solution phase synthesis. In the solid phase method, the peptide chain is sequentially constructed using a resin support, typically a benzhydrylamine resin or a chloromethylated polystyrene resin. The product is cleaved from the resin with HF and purified, generally chromatographically.

Whichever method is used, the preparation of the compounds of this invention involves the coupling of amino acids or peptide fragments by reaction of the carboxyl function of one with the amino function of another to produce an amide linkage. In order to effectively achieve coupling, it is desirable, first, that all reactive functionalities not participating directly in the reaction be inactivated by the use of appropriate blocking groups, and, secondly, that the carboxyl function which is to be coupled be appropriately activated to permit coupling to proceed. All of this involves a careful selection of both reaction sequence and reaction conditions as well as utilization of specific blocking groups so that the desired peptide product will be realized. Each of the amino acids which is employed to produce the compounds of this invention and which has the particularly selected protecting groups and/or activating functionalities is prepared by techniques well recognized in the peptide art.

Selected combinations of blocking groups are employed at each point of the total synthesis of the compounds of this invention. These particular combinations have been found to function most smoothly. Other combinations would operate in the synthesis of the compounds of this invention, although, perhaps, with a lesser degree of success. Thus, for example, benzyloxycarbonyl, t-butyloxycarbonyl, t-amyloxycarbonyl, p-methoxybenzyloxycarbonyl, adamantyloxycarbonyl, and isobornyloxycarbonyl can be variously employed as amino blocking groups in the synthesis of the compounds of this invention. Furthermore, benzyl (Bzl) generally is employed as the hydroxy-protecting group for the tyrosyl residue even though others, such as p-nitrobenzyl (PNB), p-methoxybenzyl (PMB), and the like, could well be employed.

The carboxyl blocking groups used in preparing the compounds of this invention can be any of the typical ester-forming groups, including, for example, methyl, ethyl, benzyl, p-nitrobenzyl, p-methoxybenzyl, 2,2,2-trichloroethyl, and the like.

Coupling of the suitably protected N-blocked amino acid or peptide fragment with a suitably protected carboxy-blocked amino acid or peptide fragment in preparation of the compounds of this invention consists of rendering the free carboxyl function of the amino acid or peptide fragment active to the coupling reaction. This can be accomplished using any of several well recognized techniques. One such activation technique involves conversion of the carboxyl function to a mixed anhydride. The free carboxyl function is activated by reaction with another acid, typically a derivative of carbonic acid, such as an acid chloride thereof. Examples of acid chlorides used to form mixed anhydrides are ethyl chloroformate, phenyl chloroformate, sec-butyl chloroformate, isobutyl chloroformate, pivaloyl chloride, and the like. Preferably, isobutyl chloroformate is employed.

Another method of activating the carboxyl function for the purpose of carrying out the coupling reaction is by conversion to its active ester derivative. Such active esters include, for example, a 2,4,5-trichlorophenyl ester, a pentachlorophenyl ester, a p-nitrophenyl ester, and the like. Another coupling method available for use is the well-recognized azide coupling method.

The preferred coupling method in preparation of the compounds of this invention involves the use of N,N'-dicyclohexylcarbodiimide (DCC) to activate the free carboxyl function thereby permitting coupling to proceed. This activation and coupling technique is carried out employing an equimolar quantity of DCC relative to the amino acid or peptide fragment and is carried out in the presence of an equimolar quantity of 1-hydroxybenzotriazole (HBT). The presence of HBT suppresses undesirable side reactions including the possibility of racemization.

Cleavage of selected blocking groups is necessary at particular points in the synthetic sequence employed in preparation of the compounds of this invention. A chemist of ordinary skill in the art of peptide synthesis can readily select from representative protecting groups those groups which are compatible in the sense that selective cleavage of the product can be accomplished permitting removal of one or more but less than all of the protecting groups present on the amino acid or peptide fragment. These techniques are well recognized in the peptide art. A fuller discussion of the techniques which are available for selective cleavage is provided in the literature in Schröder and Lübke, *The Peptides*, Volume I, Academic Press, New York, (1965), and especially in the Table provided at pages 72–75 thereof.

Cleavage of carboxyl protecting groups can be accomplished by alkaline saponification. Relatively strong alkaline conditions, typically using an alkali metal hydroxide, such as sodium hydroxide, potassium hydroxide, lithium hydroxide, and the like, are generally employed to deesterify the protected carboxyl. The reaction conditions under which saponification is accomplished are well recognized in the art. Many of the carboxyl blocking groups also can be removed by catalytic hydrogenolysis including, for example, hydrogenolysis in the presence of a catalyst such as palladium on carbon. Furthermore, in those instances in which the carboxyl blocking group is p-nitrobenzyl or 2,2,2-trichloroethyl, deblocking can be accomplished by reduction in the presence of zinc and hydrochloric acid.

Many of the amino blocking groups are cleaved by treating the protected amino acid or peptide with an acid such as formic acid, trifluoroacetic acid (TFA), p-toluenesulfonic acid (TSA), benzenesulfonic acid (BSA), naphthalenesulfonic acid, and the like, to form the respective acid addition salt product. Cleavage of others, for example, benzyloxycarbonyl, can be accomplished by treating the blocked amino acid or peptide with a mixture of HBr and acetic acid to produce the corresponding hydrobromide acid addition salt. The particular method or reagent which is employed will depend upon the chemical or physical characteristics of the materials involved in the specific deblocking reaction. The resulting acid addition salt can be converted to a more pharmaceutically acceptable form by treatment with a suitable ion exchange resin, such as DEAE Sephadex A25, Amberlyst A27, and the like.

The hydroxy-protecting group can be retained on the peptide throughout the sequence of its preparation, being removed during the final synthetic step in conjunction with cleavage of the amino blocking group. However, depending upon the conditions employed for removal of the carboxyl blocking group, it may be removed earlier in the preparative sequence. When the carboxyl group is cleaved by alkaline saponification, the hydroxy-protecting group is retained; however, when catalytic hydrogenolysis is employed for removal of the carboxyl protecting group, the hydroxy protecting group also is cleaved. The latter situation does not represent a serious problem since preparation of the compounds of this invention can be accomplished in the presence of a tyrosyl residue having a free hydroxyl group, for example, a tyrosyl residue.

Of the classical solution methods, a preferred specific method for preparing the compounds of this invention involves coupling a separately prepared N-terminal tripeptide with a separately prepared C-terminal dipeptide followed by appropriate deblocking of any remaining blocked moieties. The separately prepared C-terminal dipeptide which is reacted with the N-terminal tripeptide can be structured so as to contain the amide, alcohol, ether, or ester moiety. Alternatively, it can contain a group which represents a precursor to the desired C-terminal moiety. The general sequence, illustrating preparation of a pentapeptide of this invention, can be depicted as follows. In the sequence, the letter Z represents the C-terminal moiety, whether in its final form or as a precursor, the symbol AA represents an amino acid residue, and the number appended to the symbol AA represents the position of the amino acid in the ultimate peptide product sequence.

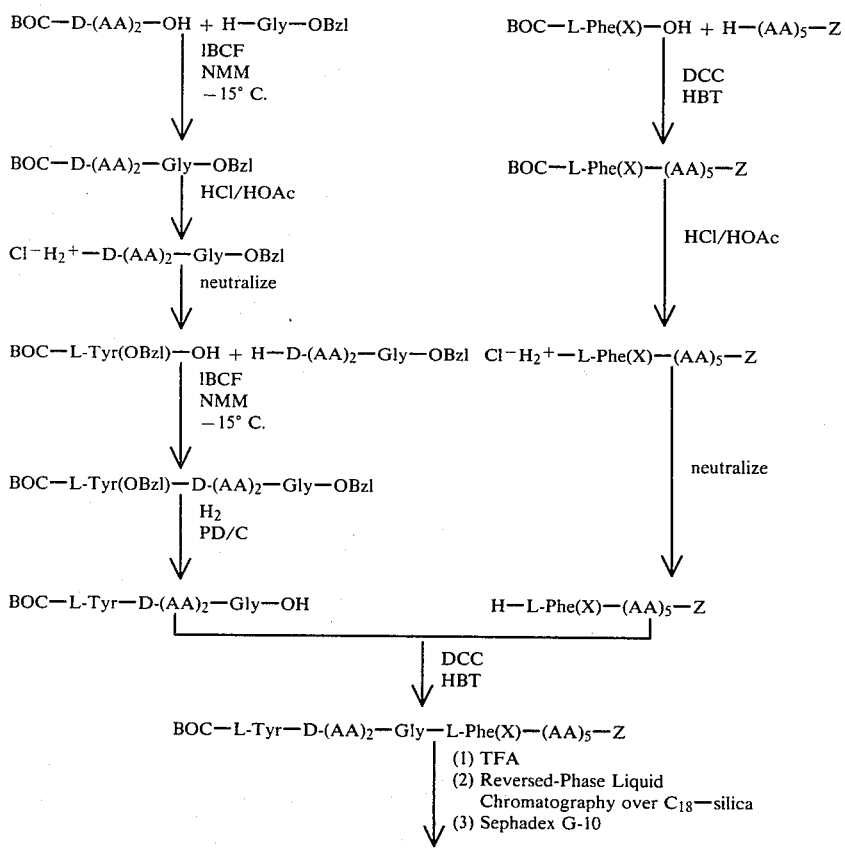

-continued

AcOH . H—L-Tyr—D-(AA)₂—Gly—L-Phe(X)—(AA)₅—Z

The above represents only one sequence for preparing compounds of this invention. Other sequences are available. Another solution method which can be employed involves the step-wise, sequential addition of single amino acids in construction of the peptide chain beginning with the C-terminal amino acid moiety. Reaction techniques such as those described above are employed in this as well as any other contemplated preparative sequence.

In certain of the compounds of this invention, one or more of the amino acid residues are substituted at the amino nitrogen by, variously, alkyl, allyl, propargyl, or cyclopropylmethyl. In these instances, the appropriate N-substituted amino acid is employed in the preparative sequence. Any of the N-monosubstituted amino acids can be prepared as follows using an N-protected amino acid as starting material:

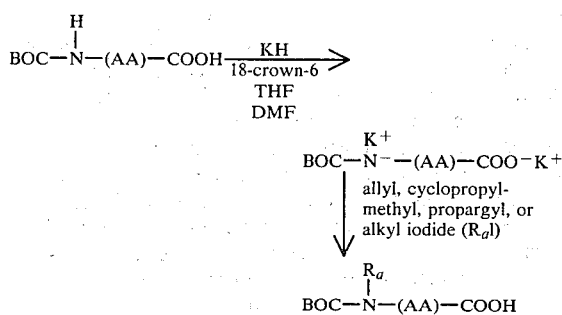

As the above sequence indicates, the amino acid first is treated with potassium hydride in the presence of a suitable crown ether to generate the dianion. The intermediate then is treated with the appropriate allyl, cyclopropylmethyl, propargyl, or alkyl iodide to obtain the desired N-substituted amino acid.

It will be apparent to those of ordinary skill in the art of peptide synethesis that racemization at the α-carbon can occur under strongly alkaline conditions such as those employed in the above alkylation procedure. The degree of racemization may vary depending upon the particular amino acid which is involved. Racemization can be minimized by using excess alkylating agent and by keeping the reaction time as short as possible. Nevertheless, even if excessive racemization does occur, the product can be purified by recrystallization as the salt of a suitable chiral amine, for example, as the salt of d(+) α-phenylethylamine.

The C-terminal portion of the peptides of this invention can be a free carboxyl. It can also be derivatized to its primary or secondary amide, ester, alcohol, or ether. In the amide pentapeptides of this invention, the amide is unsubstituted or N-monosubstituted. Derivatization to the amide is accomplished by activation of the carboxyl group of the amino acid with N,N'-dicyclohexylcarbodiimide (DCC) in the presence of 1-hydroxybenzotriazole (HBT) to give the HBT ester. The ester then is reacted with anhydrous ammonia or the appropriate primary amine to give the unsubstituted or N-monosubstituted amide. Suitable primary amines for preparation of the pentapeptides of this invention include methylamine, ethylamine, n-propylamine, and isopropylamine.

The C-terminal esters are available from the corresponding acids by techniques well recognized in the art.

Derivatization to the primary alcohol is achieved by preparing the methyl ester of the C-terminal amino acid or peptide. The ester then is reduced using sodium borohydride and lithium chloride to give the corresponding primary alcohol derivative.

The ethers can be prepared by any of a variety of well-recognized methods. One involves treating the corresponding alcohol in an aqueous sodium hydroxide medium with an alkyl bromide in which the alkyl group corresponds to the intended alkyl portion of the ether product.

The compounds of this invention are valuable pharmaceutical agents. They exhibit analgesic activity and also neuroleptic activity. They are especially useful in alleviation of pain and amelioration of emotional disturbances when administered parenterally or orally to mammals, including humans.

The compounds of this invention may be administered alone or in combination with pharmaceutically acceptable carriers, the proportion of which is determined by the solubility and chemical nature of the compound, the selected route of administration, and standard pharmaceutical practice.

Preferred compositions are those suitable for parenteral administration, that is, intramuscular, subcutaneous, or intravenous. These include sterile, injectable solutions or suspensions, and sterile injectable depot or slow-release formulations. Particularly convenient sterile, injectable solutions are made up in isotonic saline or isotonic dextrose. The sterile, injectable compositions can be prepared and stored as such or they can be prepared immediately prior to use by adding a sterile medium, for example, water, to a known weight of sterile ingredient enclosed in a vehicle, for example, a vial or an ampoule, which maintains sterility of the ingredient. The known weight of sterile ingredient may also contain sufficient sterile dextrose or sodium chloride to provide an isotonic solution or suspension after addition of the sterile medium.

Preferred compositions also are those suitable for oral administration. These can be prepared as discrete units such as capsules, tablets, and the like, each containing a predetermined amount of the active ingredient. Moreover, they, for example, can be prepared in powder or granule form, as a solution or a suspension in an aqueous or a non-aqueous medium, or as an emulsion.

The tablet can be prepared by compression, generally with one or more accessory ingredients. The tablets are prepared by compressing the active ingredient in a free-flowing form, such as a powder or granule, and generally mixed with one or more other ingredients, such as binders, lubricants, inert diluents, lubricating agents, surface active agents, buffers, flavoring agents, thickeners, preservatives, dispersing agents, and the like.

Physicians will determine the particular dosage of the compounds of this invention which is most suitable. The selected dosages will vary depending upon the mode of administration, the particular compound administered, the patient under treatment, and the kind of treatment. In general, however, the dosage will range from about 10 μg. to about 2 mg. per kilogram body weight of the recipient, and, preferably, from about 100 μg. to about 500 μg. per kilogram body weight, when administered intramuscularly or subcutaneously, and from about 1 μg. to about 200 μg. per kilogram body weight of the recipient, and, preferably, from about 3 μg. to about 50 μg. per kilogram body weight, when administered intravenously. When administered orally, the dosage generally will range from about 1 mg. to about 500 mg. per kilogram body weight of the recipient, and, preferably, from about 50 mg. to about 200 mg. per kilogram body weight, and, more preferably, from about 50 mg. to about 100 mg. per kilogram body weight.

The following examples are provided to illustrate the preparation and activity of the compounds of this invention. They are not intended to be limiting upon the scope thereof.

EXAMPLE 1

Preparation of L-Tyrosyl-D-alanyl-glycyl-L-m-bromophenylalanyl-L-(N$^\alpha$-methyl)methioninamide, Acetate Salt.

A. Trifluoroacetic Acid Salt of L-Tyrosyl-D-alanyl-glycyl-D,L-m-bromophenylalanyl-L-(N$^\alpha$-methyl)-methionyl Benzhydrylamine Resin.

The peptide-resin was synthesized by automated solid-phase synthesis in a Beckman 990 Peptide Synthesizer using 3.5 grams of benzhydrylamine resin (Beckman, 0.47 mmol-N/gram). The resin was neutralized with four percent diisopropylethylamine (DIEA) in methylene chloride and then was allowed to couple with Boc-(N-Me)Met-OH and DCC in methylene chloride to give the Boc-(N-Me)-Met-substituted resin. Boc-D,L-(m-Br)-Phe-OH, Boc-Gly-OH, Boc-D-Ala-OH, and Boc-Tyr-OH were successively incorporated onto the peptide-resin by initial coupling according to Program No. 1 and subsequent recoupling of the same amino acid according to Program No. 2. Program No. 2 was carried out once for each of the amino acids except D,L-(m-Br)Phe-OH, which was carried out three times. The resulting Boc-pentapeptide-resin was deprotected according to Steps 1–8 of Program No. 1 to give 4.04 grams of the title compound. The washes in Programs Nos. 1 and 2 were carried out at 8 ml. per gram resin.

Program No. 1

1. Wash three times with CH$_2$Cl$_2$.
2. Treat for five minutes with a 30:5:65 volume mixture of TFA:Et$_3$SiH:CH$_2$Cl$_2$.
3. Treat as in Step 2 for 30 minutes.
4. Wash twice with CH$_2$Cl$_2$.
5. Wash with methanol:CH$_2$Cl$_2$ (1:1).
6. Wash twice with methanol.
7. Wash with methanol:CH$_2$Cl$_2$ (1:1).
8. Wash twice with CH$_2$Cl$_2$.
9. Treat four times for two minutes each with 4% DIEA in CH$_2$Cl$_2$.
10. Repeat Steps 4 to 8.
11. Treat with 2.5 equivalents of the desired amino acid derivative in CH$_2$Cl$_2$ and 1.25 equivalents of DCC in CH$_2$Cl$_2$ for 120 minutes.
12. Wash four times with CH$_2$Cl$_2$.
13. Repeat Steps 5 to 7.
14. Wash three times with CH$_2$Cl$_2$.

Program No. 2

1. Treat four times for two minutes each with 4% DIEA in CH$_2$Cl$_2$.
2. Wash twice with CH$_2$Cl$_2$.
3. Wash with methanol:CH$_2$Cl$_2$ (1:1).
4. Wash twice with methanol.
5. Wash with methanol:CH$_2$Cl$_2$ (1:1).
6. Wash twice with CH$_2$Cl$_2$.
7. Wash three times with DMF:CH$_2$Cl$_2$ (1:1).
8. Treat with 2.5 equivalents of the desired amino acid derivative in DMF:CH$_2$Cl$_2$ (1:1) and 1.25 equivalents of DCC in CH$_2$Cl$_2$ for 120 minutes.
9. Wash four times with DMF:CH$_2$Cl$_2$ (1:1).
10. Repeat Steps 4 to 6.

B. Hydrogen Fluoride Salt of L-Tyrosyl-D-alanyl-glycyl-D,L-m-bromophenylalanyl-L-(N$^\alpha$-methyl)-methioninamide.

The peptide resin from Part A was reacted with liquid anhydrous HF in vacuo for 60 minutes at 0° C. with anisole as scavenger. The volatile components were removed from the reaction in vacuo, and the peptide-resin was triturated with ether and filtered to removed residual HF and anisole. The peptide was extracted from the resin by trituration with 10 percent acetic acid. The 10 percent acetic acid extract was lyophilized to yield 533 mg. of crude title compound.

C. Chromatographic Purification to Obtain Final Product.

The crude mixture of peptide diastereomers was chromatographed over a column (5×72 cm.) of reverse-phase (C$_{18}$) silica gel at low pressure (90 psig) with 28 percent acetonitrile in 0.1 N ammonium acetate. After collecting 2,000 ml. of eluant, 1.5 minute fractions of 17.1 ml. each were collected. Fractions 78–115 were pooled and lyophilized. The lyophilized product was chromatographed over a Sephadex G-10 column (2.5×100 cm.) in 0.2 N acetic acid to remove residual ammonium acetate. The fractions were lyophilized to give 198.7 mg. of the title compound as an amorphous, white solid.

$[\alpha]_D^{25}$ +20.4° (c=0.5, 1 N HCl).
$[\alpha]_{365}^{25}$ +75.4° (c=0.5, 1 N HCl).

Analysis, Calculated for C$_{31}$H$_{43}$BrN$_6$O$_8$S (739.679): C, 50.34; H, 5.96; N, 11.36; Br, 10.80. Found: C, 50.11; H, 5.56; N, 11.07; Br, 11.03.

Amino Acid Analysis:

|  | Tyr | Ala | Gly | m-BrPhe | NH$_3$ | % Peptide |
|---|---|---|---|---|---|---|
| (1) | 1.00 | 0.99 | 0.99 | 1.01 | 0.91 | 103 |
| (2) | 1.00 | 0.99 | 1.00 | 1.01 | 0.93 | 99 |

EXAMPLE 2

Preparation of L-Tyrosyl-D-alanyl-glycyl-L-m-methoxyphenylalanyl-L-(N$^\alpha$-methyl)methioninamide, Acetate Salt.

A. N$^\alpha$-t-Butyloxycarbonyl-D,L-m-methoxyphenylalanyl-L-(N$^\alpha$-methyl)methioninamide.

To a suspension of the hydrochloride salt of N$^\alpha$-methylmethioninamide (1.29 grams; 6.47 mmol) in 7.0 ml. of cold (0° C.) DMF was added DIEA (1.11 ml.; 6.47 mmol). A solution of Boc-D,L-(m-MeO)Phe-OH (1.91 grams; 6.47 mmol) in DMF (5.0 ml.) then was added to the mixture followed by HBT (1.75 grams; 12.9 mmol) and a solution of DCC (1.33 grams; 6.47 mmol) in DMF (13 ml.). The resulting mixture was stirred under a CaSO$_4$ drying tube at 0° C. for 4 hours and then at room temperature for 16 hours. The mixture was filtered to remove dicyclohexylurea (DCU), and the filtrate was evaporated in vacuo to give an orange residue. The residue was dissolved in ethyl acetate (100 ml.). The ethyl acetate layer was washed with water (3×100 ml.), pH 10 buffer (3×100 ml.), 0.1 N HCl (3×100 ml.), and water (3×100 ml.). The ethyl acetate was dried over magnesium sulfate, filtered, and the solvent was removed in vacuo to give 2.23 grams (81%) of the title compound. The material showed the presence of DCU by thin-layer chromatography (tlc).

B. D,L-m-Methoxyphenylalanyl-L-($N^\alpha$-methyl)-methioninamide, hydrochloride salt.

To a solution of the compound from Part A (2.23 grams; 5.24 mmol.) in acetic acid (10 ml.) were added anisol (1.6 ml.) and 1.62 N HCl in acetic acid (16.2 ml.). The solution was stirred under a $CaSO_4$ drying tube at room temperature (1 hour) and then was diluted with ether (470 ml.). The resulting precipitate was filtered, washed with ether (3×15 ml.) and dried in vacuo at 25° C. to give 1.53 grams (81%) of the title compound.

C. $N^\alpha$-t-Butyloxycarbonyl-L-tyrosyl-D-alanyl-glycyl-D,L-m-methoxyphenylalanyl-L-($N^\alpha$-methyl)-methioninamide.

To 7.0 ml. of dimethylformamide (DMF) were added 2.48 grams (4.2 mmol.) of Boc-L-Tyr-D-Ala-Gly-OH, dicyclohexylamine salt. The mixture was chilled in an acetone-ice bath to −10° C. To the mixture then were added 0.09 ml. (0.84 mmol.) of N-methylmorpholine and 0.55 ml. (4.2 mmol.) isobutyl chloroformate. The mixture was stirred for two minutes. To the mixture was added a chilled (−10° C.) mixture of the product from Part B (1.51 g, 4.2 mmol.) and N-methylmorpholine (0.47 ml, 4.2 mmol.) in DMF (16.5 ml.). The resulting mixture was stirred under a $CaSO_4$ drying tube in the melting ice-acetone bath (16 hr).

The mixture was filtered to remove insolubles, and the filtrate was evaporated in vacuo to give a yellow residue. The residue was partitioned between ethyl acetate (50 ml.) and water (50 ml.), and the layers were separated. The water layer was washed with ethyl acetate (3×50 ml.), and the ethyl acetate layers were combined and washed with 5% $NaHCO_3$ (3×50 ml.), 1.5 N citric acid (3×50 ml.), and water (3×50 ml.). The ethyl acetate was dried over magnesium sulfate, filtered, and the solvent was removed in vacuo to give 2.84 grams (93%) of the title compound.

D. L-Tyrosyl-D-alanyl-glycyl-D,L-m-methoxyphenylalanyl-L-($N^\alpha$-methyl)methioninamide, Trifluoroacetate Salt.

To the product from Part C (2.84 grams; 3.89 mmol.) were added anisole (3.5 ml.) and trifluoroacetic acid (35 ml.). The resulting solution was stirred under a $CaSO_4$ drying tube at room temperature for 1.25 hours after which the reaction mixture was concentrated in vacuo to a yellow oil. Ether (900 ml.) was added to the yellow oil, and the resulting precipitate was collected by filtration and dried in vacuo at 25° C. to give 2.61 grams (90%) of crude title compound.

E. Chromatographic Purification to Obtain Final Product.

The product from Part D was treated in the manner described in Part C of Example 1 to separate the two diastereomers and to obtain 758 mg. of the title compound.

$[\alpha]_D^{25}$ +25.6° (c=0.5, 1 N HCl)
$[\alpha]_{365}^{25}$ +92.9° (c=0.5, 1 N HCl)

Analysis, Calculated for $C_{32}H_{46}N_6O_9S$ (690.822): C, 55.64; H, 6.71; N, 12.17. Found: C, 55.50; H, 6.60; N, 12.32.

Amino Acid Analysis:

| Tyr | Ala | Gly | m-MeOPhe | $NH_3$ | % Peptide |
|---|---|---|---|---|---|
| 1.00 | 1.00 | 1.01 | 1.12 | 1.02 | 96 |

Other compounds that have been prepared using the procedure of Example 1 include the following:

EXAMPLE 3

L-Tyrosyl-D-alanyl-glycyl-L-m-trifluoro-methyl-phenylalanyl-L-($N^\alpha$-methyl)methioninamide, Acetate Salt.

$[\alpha]_D^{25}$ +15.29° (c=0.5, 1 N HCl).
$[\alpha]_{365}^{25}$ +56.47° (c=0.5, 1 N HCl).

Analysis, Calculated for $C_{32}H_{43}F_3N_6O_8S$ (728.794): C, 52.74; H, 5.95; N, 11.53; F, 7.82. Found: C, 53.03; H, 5.70; N, 11.72; F, 7.61.

Amino Acid Analysis:

|  | Tyr | Ala | Gly | m-$CF_3$PHe | $NH_3$ | % Peptide |
|---|---|---|---|---|---|---|
| (1) | 0.99 | 1.00 | 1.02 | 0.99 | 1.01 | 98.5 |
| (2) | 0.99 | 1.00 | 1.01 | 1.00 | 0.95 | 97.1 |

EXAMPLE 4

L-Tyrosyl-D-alanyl-glycyl-L-m-chlorophenylalanyl-L-($N^\alpha$-methyl)methioninamide, Acetate Salt.

$[\alpha]_D^{25}$ +19.67° (c=0.5, 1 N HCl).
$[\alpha]_{365}^{25}$ 69.64° (c=0.5, 1 N HCl).

Analysis, Calculated for $C_{31}H_{43}ClN_6O_8S$ (695.241): C, 53.56; H, 6.23; N, 12.09. Found: C, 53.84; H, 6.17; N, 12.31.

Amino Acid Analysis:

|  | Tyr | Ala | Gly | m-ClPhe | $NH_3$ | % Peptide |
|---|---|---|---|---|---|---|
| (1) | 1.01 | 1.00 | 0.96 | 1.04 | 1.01 | 97.4 |
| (2) | 1.00 | 1.01 | 0.99 | 1.01 | 1.02 | 98.1 |

EXAMPLE 5

L-Tyrosyl-D-alanyl-glycyl-L-m-methylphenylalanyl-L-($N^\alpha$-methyl)methioninamide, Acetate Salt.

$[\alpha]_D^{25}$ +15.01° (c=0.5, 1 N HCl).
$[\alpha]_{365}^{25}$ +53.35° (c=0.5, 1 N HCl).

Analysis, Calculated for $C_{32}H_{46}N_6O_8S$ (674.823): C, 56.96; H, 6.87; N, 12.45. Found: C, 57.18; H, 6.58; N, 12.36.

Amino Acid Analysis:

|  | Tyr | Ala | Gly | m-MePhe | $NH_3$ | % Peptide |
|---|---|---|---|---|---|---|
| (1) | 0.99 | 0.98 | 0.97 | 1.03 | 1.01 | 95 |
| (2) | 0.99 | 0.99 | 0.99 | 1.01 | 0.91 | 94 |

The analgesic activity of the compounds of this invention is demonstrated by the mouse hot plate test. In this test, an upright acrylic cylinder comprising, as its base, a hot plate surface which is maintained at 52° C. is used. A mouse (Cox Standard) is given, by subcutaneous injection, a predetermined amount of test compound dissolved or suspended in a suitable carrier, and, 15 minutes after administration of the test compound, the mouse is placed on the hot plate surface. The latency in seconds until the mouse jumps from the hot plate surface is measured. An agent which exhibits analgesic activity produces an increase in this latency over that of control mice which receive only the carrier. This must occur in a dose range which produces no motor incoordination or incapacitation. The following Table records ED$_{50}$ results obtained from this test. By the term "ED$_{50}$" is meant that dose which produces analgesia in 50% of the mice tested. Analgesia is defined as a response latency in the presence of test compound that is equal to or greater than the control response latency plus two standard deviations. The percent analgesia data are converted to probits, and the ED$_{50}$ is calculated by regression analysis of the dose-response data. Each dose response curve must have at least four points, and each point is determined using data from a minimum of ten treated mice and ten control mice.

In conjunction with the analgesic activity of the compounds of this invention, they exhibit surprisingly high levels of activity at the enkephalin ($\delta$) receptor as distinguished from the morphine ($\mu$) receptor when compared to related prior art compounds. The enkephalin ($\delta$) receptor activity is demonstrated by the recognized mouse vas deferens assay.

In the mouse vas deferens test, single mouse vas deferens from mature mice (Cox, 30-40 g.) are suspended in 3 ml. of modified Kreb's solution aerated with 95% $O_2$-5% $CO_2$ and maintained at 37° C. The twitch induced by field stimulation (0.15 Hz, 1 msec., 40 V) is recorded on a polygraph via an isometric transducer. The test compound is added to the bath in 20 to 30 $\mu$l. aliquots. A dose-response curve is constructed by cumulative addition of appropriate amounts of the compound to the bath. Comparison of relative agonist potency at the $\delta$ receptor is made on the basis of IC$_{50}$ values (concentration causing depression of 50% of the electrically evoked contraction).

The Table following also provides results for compounds of this invention when tested in the mouse vas deferens assay. The increased binding of the compounds of this invention at the enkephalin ($\delta$) receptor compared to compounds lacking ring substitution (R=H) is noteworthy and wholly unexpected.

TABLE

| H—L-Tyr—D-Ala—Gly—L-(m-R)Phe—L-(N—Me)Met—NH$_2$ | | |
|---|---|---|
| Compound R | Mouse Jump ED$_{50}$mg./kg. | Mouse vas Deferens ($\delta$ receptor) IC$_{50}$,nM |
| Br | 0.36 | 0.49 |
| Cl | 0.11 | 0.71 |
| I | —$^a$ | 2.10 |
| CF$_3$ | 0.33 | 1.78 |
| CH$_3$ | 0.33 | 2.73 |
| OMe | 0.15$^b$ | 2.92 |
| H | 0.36 | 12.2 |

$^a$Not tested
$^b$Run using Harlan ND$_4$ mice.

We claim:

1. A compound of the formula

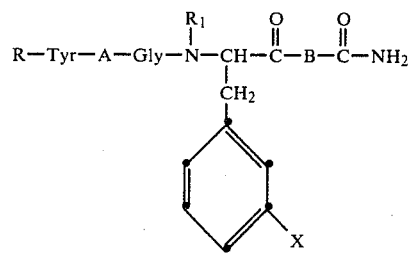

and pharmaceutically acceptable non-toxic acid addition salts thereof, in which

R is hydrogen, methyl, or ethyl;

A is the residue of a D-amino acid selected from the group consisting of Ala, Abu, Nva, Val, Nle, Leu, Ile, Gly(Al), Gly(Cp), Met, Cys(Me), Met(O), Cys(Me) (O), Ser, Thr, and Hse;

R$_1$ is hydrogen, C$_1$-C$_3$ primary alkyl, cyclopropylmethyl, allyl, or propargyl;

X is bromo, iodo, or chloro; and

B is the residue of a D- or L-amino acid lacking its carboxyl moiety and selected from the group consisting of Gly, Ala, Abu, Nva, Val, Nle, Leu, Ile, Pgl, Cys(Me), Cys(Me) (O), Cys(Me) (O$_2$), Cys(Et), Cys(Et) (O), Cys (Et) (O$_2$), Met, Met(O), Met(O$_2$), Eth, Eth(O), Eth(O$_2$), Ser(Me), Ser(Et), Hse(Me), and Hse(Et) as well as any of such residues substituted at the amino nitrogen by a C$_1$-C$_3$ primary alkyl; subject to the proviso that, when R$_1$ is other than hydrogen, B is the residue of an amino acid that lacks substitution at the amino nitrogen.

2. Compound of claim 1, in which R is hydrogen.

3. Compound of claim 1, in which A is Ala, Abu, Nva, Val, Nle, Leu, or Ile.

4. Compound of claim 3, in which A is Ala.

5. Compound of claim 1, in which A is Ser, Thr, or Hse.

6. Compound of claim 1, in which R$_1$ is C$_1$-C$_3$ primary alkyl.

7. Compound of claim 6, in which R$_1$ is methyl or ethyl.

8. Compound of claim 1, in which B is Ala, Abu, Nva, Val, Nle, Leu, or Ile, as well as any of such residues substituted at the amino nitrogen by a C$_1$-C$_3$ primary alkyl.

9. Compound of claim 8, in which B is substituted at the amino nitrogen by a C$_1$-C$_3$ primary alkyl.

10. Compound of claim 9, in which the amino nitrogen substituent is methyl.

11. Compound of claim 10, in which B is Leu.

12. Compound of claim 1, in which B is Cys(Me), Cys(Me) (O), Cys(Me) (O$_2$), Cys(Et), Cys(Et) (O), Cys(Et) (O$_2$), Met, Met(O), Met(O$_2$), Eth, Eth(O), Eth(O$_2$), Ser(Me), Ser(Et), Hse(Me), or Hse(Et), as well as any of such residues substituted at the amino nitrogen by a C$_1$-C$_3$ primary alkyl.

13. Compound of claim 12, in which B is Met unsubstituted or substituted at its amino nitrogen by a C$_1$-C$_3$ primary alkyl.

14. Compound of claim 13, in which B is Met substituted at its amino nitrogen by methyl.

15. Compound of claim 1, in which B is Pgl.

16. Compound of claim 1, in which B is substituted at its amino nitrogen by a C$_1$-C$_3$ primary alkyl.

17. Compound of claim 16, in which B is substituted at its amino nitrogen by methyl.

18. Compound of claim 1, in which B is substituted at its amino nitrogen by a $C_1$-$C_3$ primary alkyl.

19. Compound of claim 18, in which A is Ser, Thr, or Hse.

20. Compound of claim 18, in which A is Ala, Abu, Nva, Val, Nle, Leu, or Ile.

21. Compound of claim 20, in which A is Ala.

22. Compound of claim 21, in which B is substituted at its amino nitrogen by methyl.

23. Compound of claim 22, in which the chirality of the amino acid residue in Position 5 is L-.

24. Compound of claim 23, in which B is Ala, Abu, Nva, Val, Nle, Leu, or Ile.

25. Compound of claim 24, in which B is Leu.

26. Compound of claim 23, in which B is Cys(Me), Cys(Et), Met, or Eth.

27. Compound of claim 26, in which B is Met.

28. Compound of claim 27, in which X is bromo.

29. Compound of claim 27, in which X is chloro.

30. Compound of claim 27, in which X is iodo.

31. Compound of claim 2, in which B is Pgl unsubstituted at its amino nitrogen.

32. Compound of claim 31, in which A is Ala.

33. Compound of claim 32, in which $R_1$ is hydrogen.

34. Compound of claim 33, in which the chirality of the amino acid residue in Position 5 is L-.

35. Compound of claim 34, in which X is bromo.

36. Compound of claim 34, in which X is chloro.

37. Compound of claim 34, in which X is iodo.

38. Compound of claim 1, in which R is methyl.

39. Compound of claim 38, in which B is substituted at its amino nitrogen by a $C_1$-$C_3$ primary alkyl.

40. Compound of claim 39, in which A is Ser, Thr, or Hse.

41. Compound of claim 39, in which A is Ala, Abu, Nva, Val, Nle, Leu, or Ile.

42. Compound of claim 41, in which A is Ala.

43. Compound of claim 42, in which B is substituted at its amino nitrogen by methyl.

44. Compound of claim 43, in which the chirality of the amino acid residue in Position 5 is L-.

45. Compound of claim 44, in which B is Ala, Abu, Nva, Val, Nle, Leu, or Ile.

46. Compound of claim 45, in which B is Leu.

47. Compound of claim 44, in which B is Cys(Me), Cys(Et), Met, or Eth.

48. Compound of claim 41, in which B is Met.

49. Compound of claim 48, in which X is bromo.

50. Compound of claim 48, in which X is chloro.

51. Compound of claim 48, in which X is iodo.

52. Compound of claim 38, in which $R_1$ is hydrogen and B is Pgl unsubstituted at its amino nitrogen.

53. Compound of claim 52, in which the chirality of the amino acid residue in Position 5 is L-.

54. Compound of claim 53, in which A is Ala.

55. Compound of claim 54, in which X is bromo.

56. Compound of claim 54, in which X is chloro.

57. Compound of claim 54, in which X is iodo.

* * * * *